United States Patent [19]
Burton et al.

[11] Patent Number: 5,281,984
[45] Date of Patent: Jan. 25, 1994

[54] ILLUMINATION APPARATUS FOR OPHTHALMIC REFRACTORS

[75] Inventors: Roy H. Burton, Columbus; David E. Wood, Grove City, both of Ohio

[73] Assignee: R. H. Burton Company, Grove City, Ohio

[21] Appl. No.: 907,154

[22] Filed: Jul. 1, 1992

[51] Int. Cl.⁵ .............................................. A61B 3/10
[52] U.S. Cl. ................................... 351/221; 351/229; 351/234
[58] Field of Search ............... 351/220, 221, 229, 233, 351/234, 235, 216, 217; 359/742, 743; 362/29, 30, 31

[56] References Cited

U.S. PATENT DOCUMENTS

| | | | |
|---|---|---|---|
| 4,523,822 | 6/1985 | Thurston | 351/234 |
| 4,606,624 | 8/1986 | Wood | 351/234 |
| 4,798,457 | 1/1989 | Morohashi et al. | 351/234 |
| 4,820,040 | 4/1989 | Sims | 351/234 |
| 4,943,162 | 7/1990 | Sims | 351/234 |
| 5,223,864 | 6/1993 | Twisselmann | 351/233 |

Primary Examiner—Loha Ben
Attorney, Agent, or Firm—Mueller and Smith

[57] ABSTRACT

An illuminator assembly is provided for ophthalmic refractors which is formed as a singular light guide formed in unitary fashion of a transparent polymeric material. The light guide includes a light input portion located adjacent an incandescent light source mounted within the refractor housing. The light guide has transparent output portions which extend uniformly and continuously about the axis scale and further extend to the cylinder power window and the spherical power window. Through the use of a potentiometer/voltage regulator based circuit, the practitioner may alter the intensity of the light propagated to these readout functions by maneuvering a knob mounted upon the battery housing. To improve the characteristics of the illumination, the transparent outputs of the light guide are formed as Fresnel lenses.

19 Claims, 3 Drawing Sheets

ILLUMINATION APPARATUS FOR OPHTHALMIC REFRACTORS

BACKGROUND OF THE INVENTION

Correction of human vision is centered, in general, upon clinical refraction, an approach based upon optics, physiology, and the psychology of perception. Generally, any refractive analysis of the human eye has some basis in optics. For example, the treatment of defective vision will consider the position of focus of the eye which may be displaced from the emmetropic retina under conditions of either myopia or hyperopia. In addition, the eye may be astigmatic, exhibiting different focal aspects for each primary meridian which, in turn, may be oriented anywhere within a 180° aspect. Thus, the optometric clinician often is called upon to approach the optical aspect of diagnosis by evaluating the dioptric aspects of focal deficiency as they may be related to meridial power variances. The correction of occular astigmatism is carried out by collapsing the interval of Sturm with cylinder lenses. See the following publication in this regard: "Visual Optics and Refraction—A Clinical Approach" by D. D. Michaels, 2d Ed., C. V. Mosby Co., St. Louis, Mo. 1980.

Commonly, an ophthalmic instrument referred to as a refractor is employed for efficiently carrying out optical analysis. Refractors typically are fashioned comprising right and left batteries, each having an eye position for the patient before which any of a broad variety of disk-mounted testing lenses may be positioned. These lenses may be spherical, exhibiting a broad range of powers, or cylindrical, again exhibiting power variations but with respect to alignment along + and − axes.

Where an evaluation of the astigmatic eye is at hand, a broad variety of analytic approaches have been developed. Linksz has described a method for determining meridial orientation, i.e. by checking cylinder for axis and amount by rotating a correcting cylinder before the eye. See the following publications in this regard: Linksz, "A Determination of Axis and Amount of Astigmatic Error by Rotation of Trial Cylinder", *Archives of Ophthalmology*, October 1942. The rotating cylinder approach to this form of analysis was further developed into a test known as the "Jackson Cross Cylinder Test" which has been implemented broadly in ophthalmic refractors. The test is performed in both a cylinder axis and cylinder power mode. Under the test procedure, the patient is seated in a darkened examination room before the refractor and is asked to observe an illuminated distant target. The correcting cylinder axis before an appropriate eye then is manipulated by manually turning an axis control knob which is operated in conjunction with two complementary large surrounding protractor scales. Such manipulation adjusts the position of the axis of the pertinent test cylinder, its orientation is read at the scale in degrees ranging from 0° to 180°. Typically, the gradiations of the scales are arranged in steps of 5°.

Upon the axis control knob being adjusted to a first approximation, a cross-cylinder, provided as a lens consisting of equal power + and − cylinders with their axes 90° apart, is positioned at the eye station. This test lens is mounted in its loupe for rotation about a "flip" axis midway between the + and − axes. When the lens is flipped, the + and − axes change places. For this axis mode testing, the cross cylinder also is positioned with respect to a first approximation such that its axis is oriented 45° with respect to the correcting cylinder axis. Such aligning procedure is carried out somewhat semi-automatically. Generally, the refractor will carry the cross cylinder lens within a turret which is manually rotated to position the lens before the eye station or tube.

As the test continues, the cross cylinder lens is "flipped" from its first position to the alternate transverse position and the patient is asked which position is better. Depending upon the response and assuming testing is carried out with minus cylinder lenses, the correcting cylinder axis knob is manipulated to rotate the correcting cylinder toward the position at which vision is improved. These steps are repeated until a final end point is reached such that when the cross cylinder lens is flipped from one position to the other, the patient's vision is equally blurred. The practitioner then records the reading of the axis control knob by observing a painted line indicia thereon as it is positioned adjacent to a line of the earlier-described scale. Generally, the practitioner interpolates the axial orientation in degrees within 5° steps of the scale. During the procedure of gradual refinement of axis positions, the practitioner is repeatedly called upon to reference the axis scale under less than desirable ambient lighting conditions. Generally, only when the testing is completed can the light level be raised. At times, penlights have been put to use to read scales, usually only at test completion.

following the axis mode check, the cross-cylinder lens is rotated by the operator 45° to another mechanical detent control position for carrying out a cylinder power mode check. As the patient monoccularly fixates upon the illuminated target, the cross cylinder lens is flipped between alternate positions and the patient is asked, as before, at which position vision is better or worse. If vision is less blurred, correcting minus cylinder power is increased. If vision is better, the correcting cylinder power is reduced. Finally, an end point is obtained wherein correcting cylinder power is correct and the vision of the patient equally is impaired when the cross cylinder lens is flipped between its alternate positions. Readings throughout the procedure again are carried out by the practitioner under less than desirable lighting conditions.

In general, as the practitioner carries out hours of analysis with the refractor, fatigue factors and the like will set in which may lead to human error in the reading of scale based data. This, in turn, will result in lengthier tests. The provision of illuminated readouts for refraction has been suggested, for example, in U.S. Pat. No. 4,523,822 where digital readouts are provided to the practitioner through the utilization of multi-component light emitting diodes. Other attempts at improving readout have been through the uses of small pieces of plastic associated with small lightbulbs. However, the form of illumination provided by such devices has been of minimum value. In this regard, it is important, for example, that the entire axis scale be readable and that the amount of illumination supplied be as minimal as possible while remaining effective to achieve accurate recordation. Finally, it is desirable that all critical dials and readout windows be provided with efficient illumination without resort to a multitude of lighting devices and the like otherwise complicating the refractor structure.

SUMMARY

The present invention is addressed to an ophthalmic refractor and illumination apparatus therefor which provides a uniform and readily controlled light output at axis scale and power readouts during refracting procedures under conditions of lowered ambient lighting. Uniformity of illumination, particularly around the entire circular periphery of the axis scale is achieved to improve readability through the utilization of a light guide formed of transparent polymeric material which functions in conjunction with a miniature incandescent bulb light source. To enhance and control the direction of illumination, the transparent light outputs of the light guide are formed as echelon or Fresnel lenses. The light guide also includes a thin extension which carries light to a transparent output located at the spherical power readout window. As before, an echelon or Fresnel lens is employed to improve the propagation of light to this readout. Formed as an integral polymeric structure, the light guide further is fashioned having an internally disposed cavity region which permits its positioning over the gear train sequence extending from the cylinder axis control knob and the lens components located at the eye station of the refractor. Through utilization of a voltage regulator and potentiometer based control, the practitioner is provided easy adjustment of the intensity of light provided by the apparatus through manipulation of a knob at the working face of the refractor instrument. Provision of the advantageous readout light is achieved without adding bulk to the instrument.

Another feature of the invention provides an ophthalmic refractor which includes a battery housing having a patient eye position for viewing along a sight axis. A cylindrical lens assembly is incorporated with the battery which includes a plurality of movable cylinder lens components and which is actuable to position these cylinder lens components before the sight axis. A cylindrical power control knob is provided which is hand manipulated about a cylinder knob axis to selectively actuate the cylinder lens assembly. A cylinder power readout is positioned at the housing adjacent the cylinder power control knob for displaying the diopter value derived with the cylinder lens components when located at the sight axis. A cylinder axis assembly is actuable to alter the axis orientation of the cylinder lens components and a cylinder axis control knob, hand manipulated about the cylinder knob axis actuates the cylinder axis assembly. A cylinder axis scale is mounted upon the housing surrounding the cylinder axis control knob and a spherical lens assembly is provided including a plurality of movable spherical lens components selectively actuable to effect their positioning before the sight axis. A spherical power readout is positioned at the housing spaced from the cylinder axis control knob for displaying the diopter value derived with the spherical lens components by the actuation of the spherical lens assembly. An energizable light source is provided and a light guide is mounted upon the housing which is formed of transparent material having an input portion adjacent the light source for receiving light therefrom. The light guide has a first transparent output positioned substantially along the extent of the cylinder axis scale and configured to transmit light therethrough propagated from the light source. The light guide further has a second transparent output positioned in adjacency with cylinder power readout and which is configured to transmit light thereto propagated from the light source. A control arrangement effects the energization of the light source.

Another feature of the invention provides illumination apparatus for an ophthalmic refractor having a battery housing with an eye position, a cylinder lens assembly, a cylinder power readout, a cylinder axis control knob for controlling the axial orientation of the cylinder lens assembly, a cylinder axis scale with a circular periphery surrounding the cylinder axis control knob, a spherical lens assembly, and a spherical power readout. The apparatus includes a source of light energizable from a power source. Additionally, a light guide is provided which is formed of transparent polymeric material having a light output portion for receiving light from the source, an integrally formed first transparent output positioned at and substantially coextensive with the cylinder axis scale circular periphery and configured to transmit light for illuminating the scale which is propagated from the source. The light guide further has a second transparent output integrally formed therewith and extending to the cylinder power readout and which is configured to transmit light for illuminating the cylinder power readout and which is propagated from the source. A control arrangement selectively energizes the source of light.

Other objects of the invention will, in part, be obvious and will, in part, appear hereinafter.

The invention, accordingly, comprises the apparatus possessing the construction, combination of elements, and arrangement of parts which are exemplified in the following detailed disclosure.

For a fuller understanding of the nature and objects of the invention, reference should be had to the following detailed description taken in connection with the accompanying drawings.

DETAILED DESCRIPTION OF THE INVENTION

Figure 1:
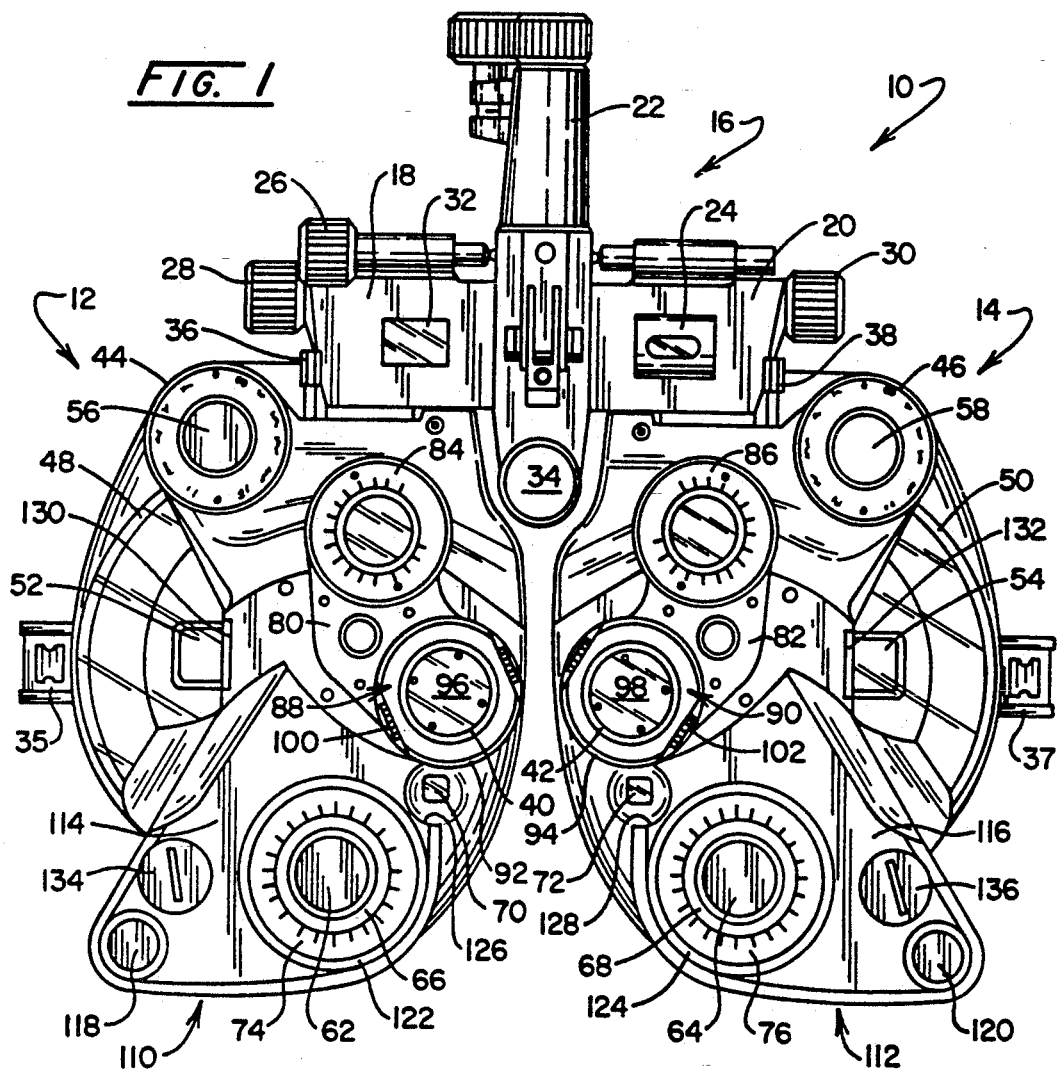
FIG. 1 is a front view of a refractor structured in accordance with the invention.

Referring to FIG. 1, a refractor is depicted generally at 10 as is observed typically from a practitioner's position. Refractor 10 includes two substantially identical but mirror image batteries, a right eye battery being represented at 12 and a left eye battery being represented at 14. These batteries 12 and 14 are supported by a bridging structure represented generally at 16 having components 18 and 20 which, in turn, are coupled to a yoke 22. The yoke 22 is coupled to a refractor arm (not shown), in turn, supported by an ophthalmic instrument stand (not shown). Various eyespan and leveling adjustments are provided within the bridging structure 16. For example, leveling utilizing a bubble level at 24 is carried out by adjusting knob 26; pupilary distance (PD) is adjusted by co-rotating knobs 28 and 30 providing a readout at 32; cornea distance is adjusted with a patient forehead rest 33 (FIG. 2) which is adjusted with knob 34; (FIG. 1) using prisms as at 35 and 37 and the convergence orientation of batteries 12 and 14 can be adjusted by respective levers 36 and 38.

As described in detail, for example, in U.S. Pat. Nos. 3,498,699; and 4,606,624 incorporated herein by reference, each battery of the refractor 10 carries a collection of lenses which are supported within rotatable disks which a practitioner may position in alignment with viewing tubes or patient eye positions through which the patient views along a sight axis. These viewing tubes are located at 40 within battery 12 and at 42 within battery 14.

Spherical lenses are maneuvered before the eye station of the patient at 40 and 42, first through adjustment of a strong sphere lens knob at 44 in the case of battery 12 and at 46 for the case of battery 14. These adjustments provide, for example, three diopter increments. Spherical power is more finely adjusted, for example, by ¼ diopter increments at an outwardly disposed portion of a lens disk as at 48 in the case of battery 12 and 50 in the case of battery 14. A spherical power readout for the spherical lens assembly adjusted by knob 44 and disk 48 as well as knob 46 and disk 50 is provided at window 52 for the case of battery 12 and window 54 for the case of battery 14. Positioned coaxially on each of the strong sphere knobs 44 and 46 is an auxiliary lens control knob shown, respectively, at 56 and 58 which serve to position filters and the like before the sight axes of the device 10.

Each of the batteries 12 and 14 also contains a cylinder lens assembly formed of two disks, one such disk carrying a stronger collection of cylinder lenses about its periphery, and the other carrying a collection of weaker cylinder lenses such that they may be combined in a progressive power sequence through interconnection with a Geneva intermittent drive. This Geneva drive is manipulated by the practitioner at a control knob as shown at 62 on battery 12 and at 64 on battery 14. While the control knobs 62 and 64 serve to position successive cylinder lenses before respective viewing tubes 40 and 42, the cylinder axis for each such positioned cylinder lens may be controlled by rotative manipulation of an axis control knob 66 at battery 12 and of an axis control knob 68 at battery 14. Cylinder power readouts identifying the cylinder lenses of the associated disk assembly are set forth in numeric fashion at a small interior cylinder power readout window at 70 in the case of battery 12 and at 72 in the case of battery 14. Note that these windows 70 and 72 are spaced from but adjacent the respective cylinder power control knobs 62 and 64. The windows additionally may be seen to be somewhat indented or depressed within the housing structure for the two batteries 12 and 14.

The cylinder axis for each cylinder lens positioned before the eye stations at viewing axes or tubes 40 and 42 may be altered by rotative manipulation of outer knobs 66 and 68 through reading a protractor type scale surrounding these knobs. In this regard, an axis scale to be read by the practitioner is located at 74 in the case of knob 66 and at 76 in the case of knob 68. Generally, these scales 74 and 76 will carry dual, protractor forms of indicia in degrees from 0 to 180 which are read in conjunction with a pointer painted on the control knobs. Typically, such scales are graduated in 5° increments, the practitioner interpolating between indicia marks.

The above-described Jackson cross cylinder test conventionally is carried out using a cross cylinder lens mounted upon a rotative lens mount which, in turn, is supported upon a pivotal bi-loupe turret. One such turret is pivotally mounted on each battery of the refractor 10 in a manner such that the practitioner rotates the turret to an orientation wherein the cross-cylinder lens is aligned with an associated battery viewing tube. FIG. 1 shows a turret 80 pivotally mounted upon battery 12 and a corresponding turret 82 mounted upon battery 14. Turrets 80 and 82 each support a rotary prism lens system shown, respectively, at 84 and 86, as well as a cross-cylinder assembly shown, respectively, at 88 and 90. Each of the assemblies 88 and 90 includes a rotatable lens mount, shown, respectively, at 92 and 94. Cross cylinder lenses 96 and 98 may be pivotally rotated about a flip axis by the manual movement of the pivoting assembly extending to oppositely disposed knurled knobs as shown at 100 in conjunction with lens 96 and at 102 in conjunction with lens 98. Generally, the axial orientation of the cross cylinder lens is synchronized with the cylinder axis positioned before an associated viewing tube by virtue of a geared connection of both with axis control knobs 66 and 68. Thus, as noted earlier, during the performance of the Jackson cross cylinder test, the practitioner flips the lenses as at 96 and 98 depending upon the eye being examined. While this is carried out, an associated scale as at 74 or 76 is observed and interpreted during a progressive refinement procedure.

Figure 2:
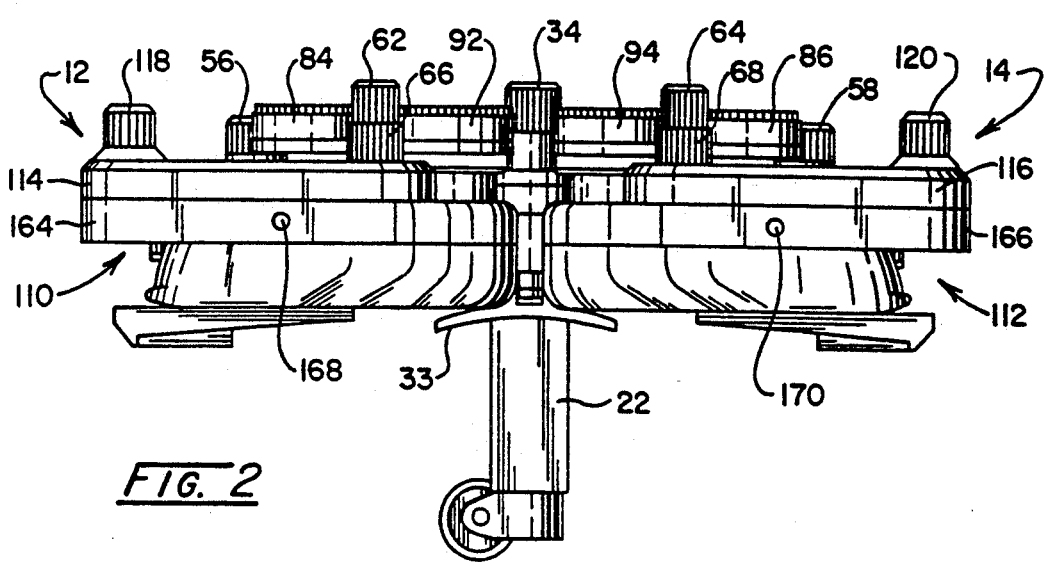
FIG. 2 is a bottom view of the refractor of FIG. 1.

Looking additionally to FIG. 2, it may be observed that the housing of each battery 12 and 14 extends somewhat outwardly at the lower regions thereof, for example, at 110 in the case of battery 12 and at 112 in the case of battery 14. These extensions include an upwardly disposed metal cover as at 114 in the case of battery 12 and as at 116 in the case of battery 14. Cover 114 cooperates with a rear cover 164, while cover 116 cooperates with a rear cover 166. These covers, inter alia, support a light source switch and intensity adjustment knob as at 118 in the case of battery 12 and 120 in the case of battery 14. Knobs 118 and 120 form the control feature of a selective illumination system wherein through employment of a light guide, light is propagated from a light source to a transparent output as at 122 in the case of battery 12 and as at 124 in the case of battery 14. It may be observed that the output periphery 122 fully surrounds scale 74 at battery 12 as does output 124 with respect to scale 76 at battery 14. The light guide based illumination system also extends to a transparent output at 126 in the case of battery 12 and at 128 in the case of battery 14. Transparent output 126 surmounts about one-half of the peripheral extent of cylinder power readout window 70, while transparent output 128 similarly surmounts cylinder power readout window 72 at battery 14. The light guide system further extends to transparent outputs 130 and 132 respectively serving to illuminate the spherical power readouts at windows 52 and 54. Access to the incandescent bulb form of light source used in conjunction with the light guides is made through a wide screw plug as at 134 in the case of battery 12 and as at 136 in the case of battery 14.

Figure 3:
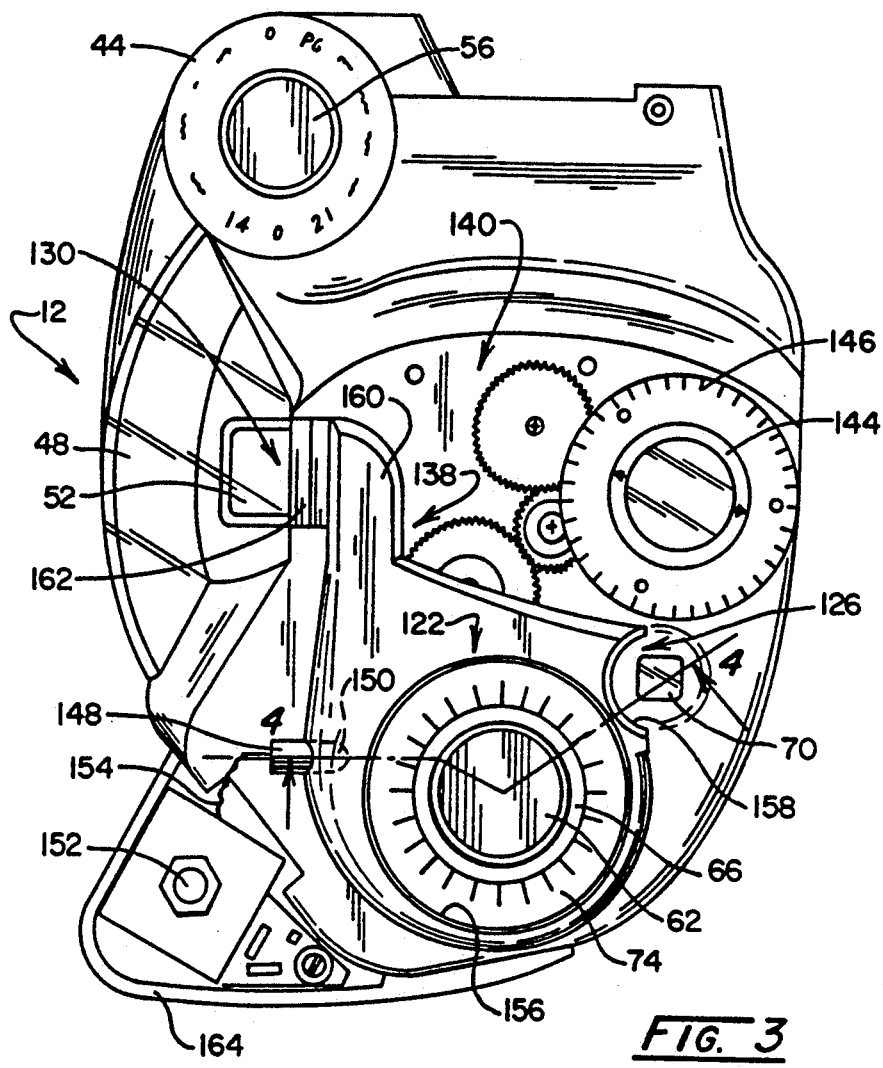
FIG. 3 is a partial front view of one battery of the refractor of FIG. 1 with portions broken away to reveal internal structure.
Figure 4:
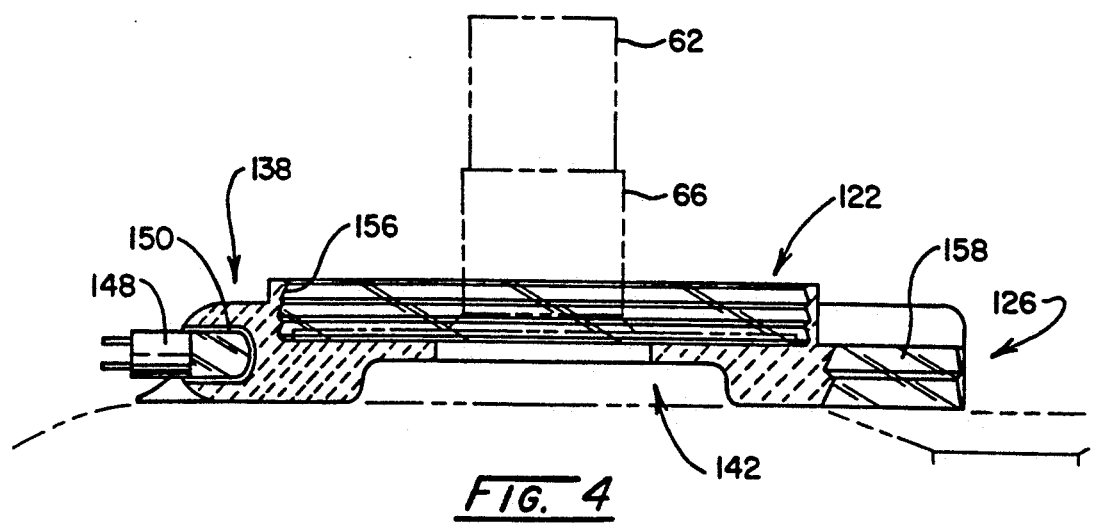
FIG. 4 is a partial sectional view of the refractor battery shown in FIG. 3 taken through the plane 4—4 thereof.

Looking to FIGS. 3 and 4, the battery 12 is shown with the metal cover 114 removed to reveal the light guide therewithin represented generally at 138. A similar light guide design which is a mirror image of light guide 138 is positioned within battery 14. Light guide 138 extends over a gear train sequence represented at 140 and thus, as seen in FIG. 4, is formed having a cavity 142 extending inwardly from its bottom surface as seen in FIG. 4. This accommodates the gear train sequence 140 which functions in conjunction with axis knob 66 to rotate an auxiliary lens holder or aperture ring 144 at the sight axis or viewing tube 40. An additional axis scale 146 surmounts lens holder 144 such that the pointers at the latter device will track or simultaneously emulate the axis position selected by the operator with respect to scale 74. Light guide 138 is formed of a clear light propagating polymeric material such as an acrylic, ABS, transparent polystyrene, polyester, polycarbonate, and PET plastic, device 138 is coated with a reflective material such as aluminum at all surfaces except the transparent outputs as at 122, 126, and 130. The light source for light guide 138 is a small light bulb 148 which is seen to be mounted horizontally within a light receiving cavity 150 formed within one side of light guide 138. Bulb 148 may be provided, for example, as a bi-pin type 7349 miniature bulb produced by Sylvania Electric Company. Such bulbs, conventionally, are rated at 6.3 V, 200 ma, and exhibit about 0.55 to 0.6 candella M.S.C.P. (mean spherical candlepower). The output of bulb 148 is variable in intensity so as to adjust the corresponding intensity of the outputs at the transparent outputs 122, 126, and 130. This adjustment is provided by a switching potentiometer shown in FIG. 3 at 152, the connection between device 152 and associated circuit components and the bulb 148 being represented at lead 154. Device 152 is rotationally actuated by the operator by appropriate turning or adjusting of knob 118. A corresponding adjustment of knob 120 in battery 14 provides the same function. (See FIG. 1). As noted earlier, bulbs 148 are accessible by the practitioner from the front of battery 12 by simple removal of a wide access screw 134 as described in conjunction with FIG. 1. A similar access to a corresponding bulb within battery 14 is provided from screw cover 136.

Figure 5:
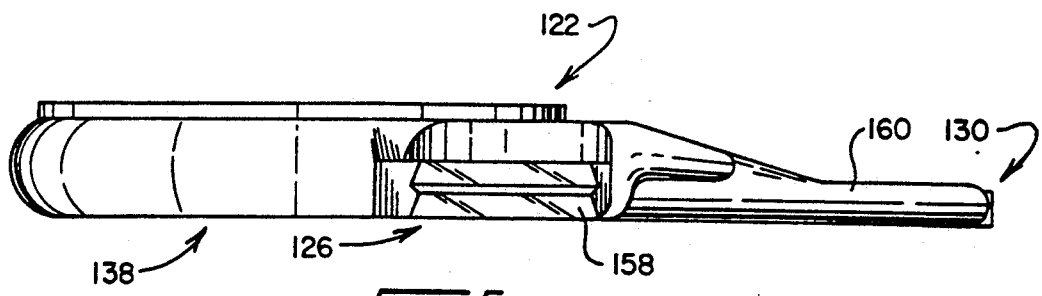
FIG. 5 is a right side view of a light guide incorporated within FIG. 3.
Figure 6:
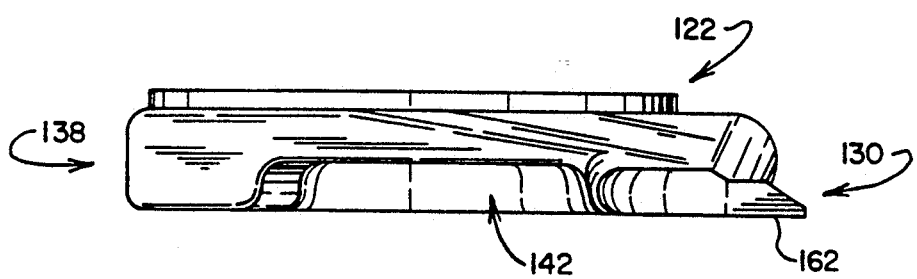
FIG. 6 is a top view of the light guide of FIG. 5.

In order to assure appropriate lighting at windows 70 and 52 and, quite importantly, the axis scale 74, light guide 138 is configured having a three element echelon or Fresnel lens extending entirely about the axis scale 74 at its transparent output 122. This Fresnel lens is seen additionally in FIG. 4 at 156. In similar fashion, to assure appropriately downwardly directed and controlled illumination at window 70, a two element Fresnel lens 158 is provided as seen in FIG. 4. FIG. 5, a side view taken in a right-to-left sense with respect to FIG. 3 also reveals this dual element lens 158. In the latter figure, it may be observed that the light guide 138 transforms into a thin cross section or dimension at its uppermost region 160. This region then transforms to a light projecting or output surface configured to illuminate spherical power window 52.

FIGS. 1 through 3 show that the illuminational system of the instant embodiment includes earlier described metal covers 114 and 116. These covers additionally cooperate with earlier noted lower disposed back cover as shown, respectively, at 164 and 166 in FIG. 2. Small openings are provided in the latter back covers 164 and 166 as shown, respectively, at 168 and 170 to permit conventional tension adjustment of the detent components of the spherical lens disks of batteries 12 and 14. Back covers 164 and 166 preferably are replaced by an integrally molded structuring of the housings of the batteries 12 and 14.

Figure 7:
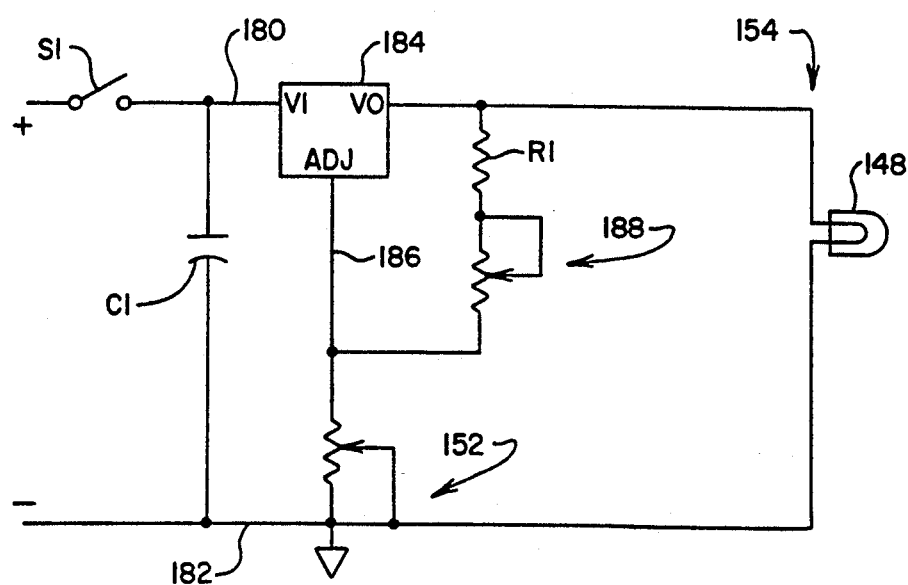
FIG. 7 is an electrical schematic drawing of a circuit employed with the system of the invention.

Looking to FIG. 7, an electric circuit for adjusting the luminous intensity of the bulbs used with the system of the invention as at 148 is revealed. In general, mean spherical candle power is directly proportional to the 3.5 power of applied voltage. Accordingly, the circuit is seen to include a switching function represented at S1 in conjunction with lines 180 and 182. Across these lines there is provided a filtering capacitor C1 and line 180 additionally is seen to incorporate a voltage regulator 184. Regulator 184 may be provided, for example, as a type LM317-T having an ADJ terminal coupled via line 186 to potentiometer 152. The latter device may be provided as a 1K ohm potentiometer with a switch the function of which is described at S1, for example, a type 85R2A-R5A-AIOR51 marketed by Bourns Electric Company. A trim potentiometer utilized to calibrate for maximum bulb voltage is provided at 186 in conjunction with resistor R1. The latter device may be provided, for example, as a type EVM-SZ0GAO1B22, 200 ohm potentiometer marketed by Panasonic, Inc.

Since certain changes may be made in the above-described apparatus without departing from the scope of the invention herein involved, it is intended that all matter contained in the description thereof or shown in the accompanying drawings shall be interpreted as illustrative and not in a limiting sense.

I claim:
1. An ophthalmic refractor, comprising:
   a battery housing having a patient eye position for viewing along a sight axis;
   a cylinder lens assembly including a plurality of movable cylinder lens components actuable to position said cylinder lens components before said sight axis;
   a cylinder power control knob, hand manipulative about a cylinder knob axis to selectively actuate said cylinder lens assembly;
   a cylinder power readout positioned at said housing adjacent said cylinder power control knob for displaying the diopter value derived with said cylinder lens components when located at said sight axis;
   a cylinder axis assembly actuable to alter the axis orientations of said cylinder lens components;
   a cylinder axis control knob, hand manipulative about said cylinder knob axis to actuate said cylinder axis assembly;
   a cylinder axis scale mounted upon said housing and surrounding said cylinder axis control knob;
   a spherical lens assembly including a plurality of movable spherical lens components, selectively actuable to effect their positioning before said sight axis;
   a spherical power readout positioned at said housing spaced from said cylinder axis control knob for displaying the diopter value derived with said spherical lens components by actuation of said spherical lens assembly;
   an energizable light source;
   a light guide mounted upon said housing, formed of transparent material, having an input portion adjacent said light source for receiving light therefrom, having a first transparent output positioned substantially along the extent of said cylinder axis scale and configured to transmit light thereto propagated from said light source, and having a second transparent output positioned in adjacency with said cylinder power readout and configured to transmit light thereto propagated from said light source; and control means for effecting energization of said light source.

2. The refractor of claim 1 in which said light guide includes a third transparent output positioned in adjacency with said spherical power readout and configured to transmit light thereto propagated from said light source.

3. The refractor of claim 1 in which said light guide first transparent output is configured as an echelon lens of circular periphery fully encircling said cylinder axis scale.

4. The refractor of claim 1 in which said light guide first transparent output is configured as a three element Fresnel lens of circular peripheral extent substantially encircling said cylinder axis scale.

5. The refractor of claim 1 in which said light guide first transparent output is configured as a Fresnel lens of circular peripheral extent substantially encircling said cylinder axis scale; and said second transparent output is configured as a Fresnel lens configured to illuminate said cylinder power readout.

6. The refractor of claim 1 in which said light guide includes a third transparent output positioned in adjacency with said spherical power readout, configured as a Fresnel lens transmitting light thereto propagated from said light source.

7. The refractor of claim 6 in which said first transparent output is a three-element Fresnel lens, and said second and third transparent outputs are two-element Fresnel lenses.

8. The refractor of claim 1 in which:
said cylinder axis assembly includes a gear sequence extending from said cylinder axis control knob to said patient eye position; and
said light guide is integrally formed of transparent polymeric material and includes an inwardly extending cavity for receiving at least a portion of said gear sequence.

9. The refractor of claim 8 in which:
said light source is an incandescent lamp; and
said light guide input portion is configured as a lamp receiving cavity for receiving said lamp in light transfer relationship.

10. The refractor of claim 8 in which said light guide includes an integrally formed thin portion extending outwardly from said inwardly extending cavity portion to a third transparent output positioned in adjacency with said spherical power readout and configured to transmit light thereto propagated from said light source.

11. The refractor of claim 10 in which said first, second and third transparent outputs are each configured as a Fresnel lens.

12. The refractor of claim 1 in which:
said light source is an incandescent lamp; and
said control means includes a voltage regulator having an output coupled with said lamp and connectable with a source of power, switching means actuable to apply power from said source of power to said voltage regulator, a potentiometer coupled with said lamp and the output of said voltage regulator, rotatably actuable to selectively adjust the value of voltage applied to said lamp; and
including a light control knob mounted upon said housing and operatively coupled with said potentiometer to effect actuation thereof.

13. Illuminator apparatus for an ophthalmic refractor having a battery housing with an eye position, a cylinder lens assembly, a cylinder power readout, a cylinder axis control knob for controlling the axial orientation of said cylinder lens assembly, a cylinder axis scale with a circular periphery surrounding said cylinder axis control knob, a spherical lens assembly, and a spherical power readout, comprising:

a source of light energizable from a power source;
a light guide formed of transparent polymeric material, having a light input portion for receiving light from said source, an integrally formed first transparent output positioned at and substantially coextensive with said cylinder axis scale circular periphery and configured to transmit light for illuminating said scale which is propagated from said source, said light guide having a second transparent output integrally formed therewith and extending to said cylinder power readout and configured to transmit light for illuminating said cylinder power readout which is propagated from said source; and
control means for selectively energizing said source of light.

14. The illumination apparatus of claim 13 in which said light guide includes an integrally formed third transparent output extending to an adjacency with said spherical power readout and configured to transmit light thereto propagated from said light source.

15. The illumination apparatus of claim 13 in which said first and second transparent outputs are each configured as a Fresnel lens.

16. The illumination apparatus of claim 13 in which said first transparent output is configured as a three-element Fresnel lens and said second transparent output is configured as a two-element Fresnel lens.

17. The illumination apparatus of claim 16 in which said light guide includes an integrally formed third transparent output configured as a Fresnel lens and extending to an adjacency with spherical power readout and configured to transmit light thereto propagated from said light source.

18. The illumination apparatus of claim 17 in which said light guide transparent polymeric material is coated with a light reflecting metallic material at all surface regions extending to said first, second and third transparent outputs.

19. The illumination apparatus of claim 13 in which:
said light source is an incandescent lamp; and
said control means includes a voltage regulator having an output coupled with said lamp and connectable with a source of power, switching means actuable to apply power from said source of power to said voltage regulator, a potentiometer coupled with said lamp and the output of said voltage regulator, rotatably actuable to selectively adjust the value of voltage applied to said lamp; and
including a light control knob mounted upon said housing and operatively coupled with said potentiometer to effect actuation thereof.

* * * * *